United States Patent
Yeisley et al.

(10) Patent No.: US 7,999,121 B2
(45) Date of Patent: Aug. 16, 2011

(54) DERIVATIZED 3,4-ALKYLENEDIOXYTHIOPHENE MONOMERS, METHODS OF MAKING THEM, AND USE THEREOF

(75) Inventors: Shawn Yeisley, Newport, DE (US); Charles J. Dubois, Wilmington, DE (US); Che-Hsiung Hsu, Wilmington, DE (US); Steven W. Shuey, Landenberg, PA (US); Yulong Shen, Greenville, DE (US); Hjalti Skulason, Buelton, CA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/903,356

(22) Filed: Oct. 13, 2010

(65) Prior Publication Data
US 2011/0024693 A1 Feb. 3, 2011

Related U.S. Application Data

(62) Division of application No. 11/721,743, filed as application No. PCT/US2005/047188 on Dec. 23, 2005, now Pat. No. 7,838,688.

(60) Provisional application No. 60/640,563, filed on Dec. 30, 2004, provisional application No. 60/694,393, filed on Jun. 27, 2005.

(51) Int. Cl.
*C07D 495/02* (2006.01)
*C07D 333/50* (2006.01)
*C08G 75/32* (2006.01)

(52) U.S. Cl. ............. 549/50; 549/62; 528/377; 528/380

(58) Field of Classification Search .................. None
See application file for complete search history.

(56) References Cited

U.S. PATENT DOCUMENTS

| | | | |
|---|---|---|---|
| 4,959,430 A | 9/1990 | Jonas et al. | |
| 4,987,042 A | 1/1991 | Jonas et al. | |
| 5,035,926 A | 7/1991 | Jonas et al. | |
| 6,150,426 A | 11/2000 | Curtin et al. | |
| 6,303,328 B1 | 10/2001 | Thompson et al. | |
| 6,391,481 B1 | 5/2002 | Jonas et al. | |
| 7,102,016 B2 | 9/2006 | Reuter | |
| 7,202,369 B2 | 4/2007 | Baik et al. | |
| 7,318,982 B2 | 1/2008 | Gozdz et al. | |
| 7,341,801 B2 | 3/2008 | Reuter et al. | |
| 2001/0019782 A1 | 9/2001 | Igarashi et al. | |
| 2003/0176628 A1 | 9/2003 | Groenendaal et al. | |
| 2004/0072987 A1 | 4/2004 | Groenendaal et al. | |
| 2004/0147765 A1 * | 7/2004 | Baik et al. | 549/62 |
| 2004/0254297 A1 | 12/2004 | Hsu et al. | |
| 2005/0272214 A1 | 12/2005 | Chiang et al. | |
| 2009/0318710 A1 * | 12/2009 | Brassat et al. | 549/50 |

FOREIGN PATENT DOCUMENTS

| | | |
|---|---|---|
| EP | 1191612 | 3/2002 |
| EP | 1191614 | 3/2002 |
| WO | WO 00/70655 | 11/2000 |
| WO | WO 01/41512 | 6/2001 |
| WO | WO 02/02714 | 1/2002 |
| WO | WO 02/15645 | 2/2002 |

OTHER PUBLICATIONS

Campbell et al., "Excitation Transfer Processes in a phosphor-doped poly (p-phenylene vinylene) Light-Emitting Diode" Physical Review B, Feb. 8, 2002, 65, 085210-1-085210-8.
Caras-Quintero et al., "Efficient Synthesis of 3,4-Ethylenedioxythiophenes (EDOT) by Mitsunobu Reaction", The Royal Society of Chemistry, Oct. 16, 2002, 2690-2691.
Gustafsson et al., "Flexible Light-Emitting Diodes made from Soluble Conducting Polymer", Letters to Nature, Jun. 11, 1992, 357, 477-479.
Kirk-Othmer, (Howe-Grant, Ed.), "Photoconductive Polymers", Encyclopedia of Chemical Technology (4th Ed), 1996, 18, 837-860.
Laha et al., "Highly Selective Epoxidation of Olefinic Compounds over TS-1 and TS-2 Redox Molecular Sieves Using Anhydrous Urea-Hydrogen Peroxide as Oxidizing Agent", Journal of Catalysis, Feb. 25, 2002, 208(2), 339-344.
Lima, "Electropolymerization of and 3,4-ethylenedioxtyiophene and 3,4-Ethylenedioxythiophene Methanol in the Presence of Dodecylbenezenesulfonate", Synthesis Metals, 1998, 93, 33-41.
O'Brien et al., "Electrophosphoresence from a Doped Polymer Light Emitting Diode", Synthetic Metals, 2001, 116(1-3), 379-383.
Schottland et al., "Synthesis and Polymerization of New Monomers Derived from 3,4-Ethylenedioxythiophene", J. Chim. Phys., 1998, 95, 1258-1261.
Segura et al., "Synthesis and Electropolymerization of a Perylenebisimide-Functionalized 3,4-Ethylenedioxythiophene (EDOT) Derivative", Organic Letters, Mar. 18, 2005, 7(12), 2345-2348.
Venturello et al., "A Convenient Catalytic Method for the Dihydroxylation of Alkenes by Hydrogen Peroxide", Synthesis, Apr. 1989, 4, 295-297.

* cited by examiner

*Primary Examiner* — Kamal Saeed
*Assistant Examiner* — Nyeemah A Grazier
(74) *Attorney, Agent, or Firm* — Woodcock Washburn LLP

(57) ABSTRACT

The present invention relates to methods of making derivatized 3,4-alkylenedioxythiophene monomers and methods of using the 3,4-alkylenedioxythiophene monomers.

4 Claims, 1 Drawing Sheet

DERIVATIZED 3,4-ALKYLENEDIOXYTHIOPHENE MONOMERS, METHODS OF MAKING THEM, AND USE THEREOF

CROSS-REFERENCE TO RELATED APPLICATIONS

This application is a divisional of U.S. Ser. No. 11/721,743 filed May 7, 2008 which is the National Stage of International Application No. PCT/US2005/047188, filed Dec. 23, 2005 which claims the benefit of U.S. Provisional Application Ser. No. 60/694,393 filed on Jun. 27, 2005 and U.S. Provisional Application Ser. No. 60/640,563 filed on Dec. 30, 2004, each of which is incorporated herein by reference in its entirety.

FIELD OF THE DISCLOSURE

The present invention is directed to processes for preparing derivatized 3,4-alkylenedioxythiophenes having improved solubility in water, methods of making them, and their use in electrical devices.

BACKGROUND

Poly(3,4-ethylenedioxythiophene) (PEDOT) is an important electrically conductive polymer because of both its high conductivity and temperature stability. Its monomeric unit, 3,4-ethylenedioxythiophene (EDOT), however, has poor solubility in water. While some water-soluble EDOT compounds are known in the art, such as EDOT-CH$_2$OH, the known method of making EDOT-CH$_2$OH involves a complex series of six reaction steps starting from thiodiglycolic acid. Thus, a need exists for improved processes for making derivatized EDOT compounds having improved solubility in water.

SUMMARY

Provided are methods of making derivatized 3,4-alkylenedioxythiophene compounds.

In one embodiment, the present invention comprises a process for preparing a compound of Formula I:

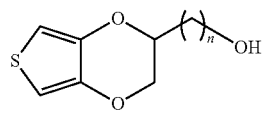

Formula I wherein n is from 1 to 4, comprising contacting a compound of Formula II:

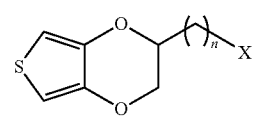

Formula II wherein X is halogen and n is from 1 to 4; with an inorganic hydroxide, an alkali or alkaline earth metal carboxylate, an ammonium or alkylammonium carboxylate, an alkali or alkaline earth metal alkoxide, or an ammonium or alkylammonium alkoxide.

The

of Formula II can be a straight chain or branched. In some embodiments, the group can be substituted with moieties which do not interefere with the chemistry in the process for forming the compound with Formula I. In some embodiments, the substituents may also improve solubility, such as, for example, ether, ester, or carboxylate groups.

In one embodiment, the present invention comprises a process for preparing a compound of Formula II:

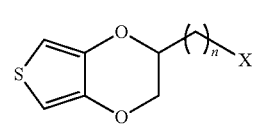

Formula II comprising contacting a 3,4-dialkoxythiophene with an ω-halo-1,2-alkanediol in the presence of an acid. In certain embodiments, the ω-halo-1,2-alkanediol is a 3-halo-1,2-propanediol.

In one embodiment, the present invention comprises a process for preparing a compound of Formula V:

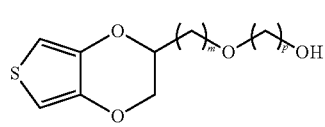

Formula V wherein m is 1 or 2 and p is 2 or 3, comprising contacting a compound of Formula VI:

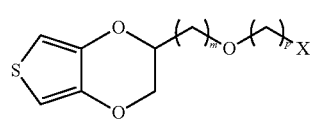

Formula VI wherein X is halogen, m is 1 or 2 and p is 2 or 3; with an inorganic hydroxide, an alkali or alkaline earth metal carboxylate, an ammonium or alkylammonium carboxylate, an alkali or alkaline earth metal alkoxide, or an ammonium or alkylammonium alkoxide.

The foregoing general description and the following detailed description are exemplary and explanatory only and are not restrictive of the invention, as defined in the appended claims

BRIEF DESCRIPTION OF THE DRAWINGS

Embodiments are illustrated in the accompanying figures to improve understanding of concepts as presented herein.

Figure 1:
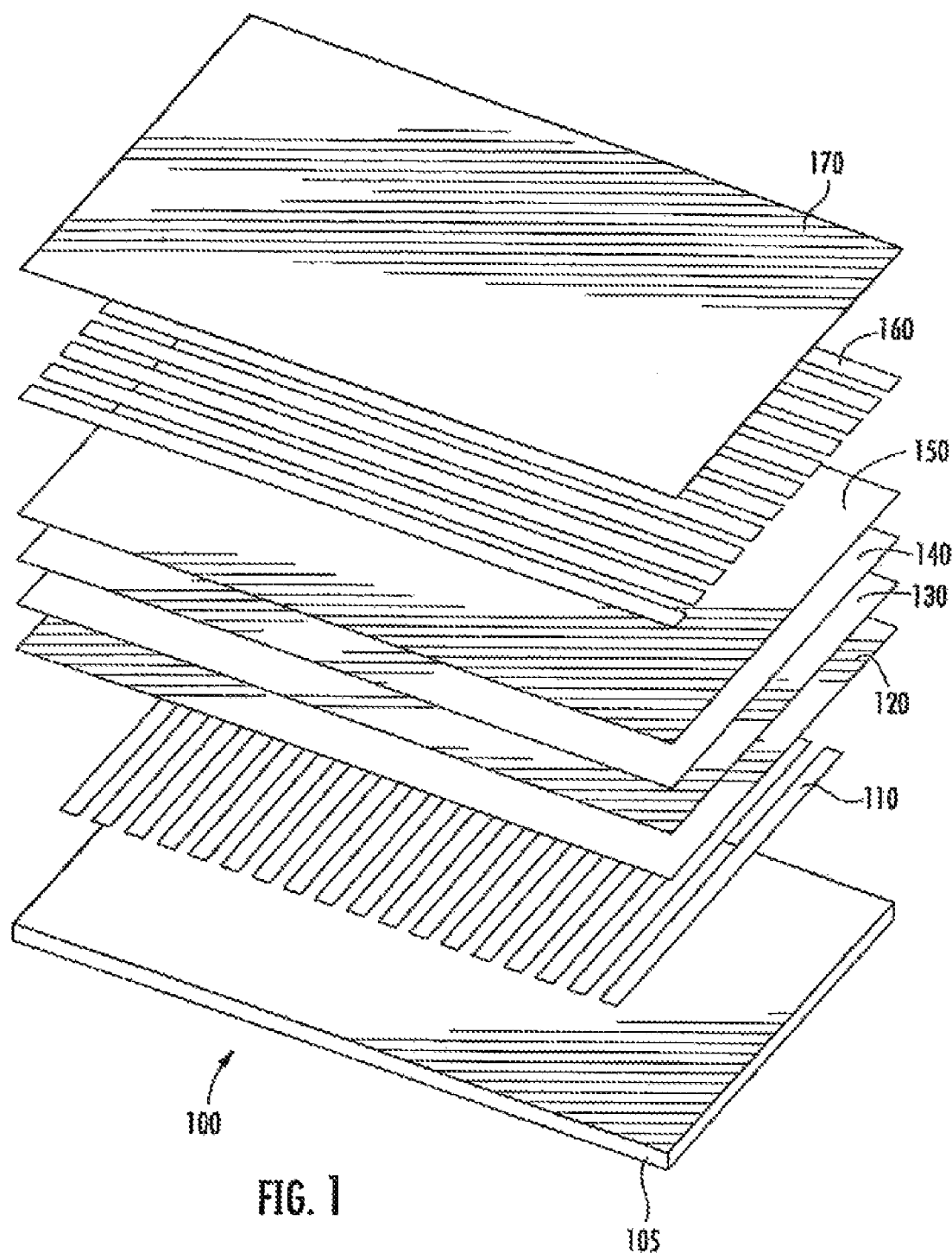
FIG. 1 includes an illustration of an exemplary organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Provided are processes for preparing derivatized 3,4-alkylenedioxythiophene compounds, the products produced by the processes, electronically conductive polymer compositions comprising derivatized 3,4-alkylenedioxythiophene monomers, and devices thereof. An exemplary derivatized 3,4-alkylenedioxythiophene compound of the present invention is (2,3-dihydrothieno[3,4-b][1,4]dioxin-3-yl)methanol, or EDOT-CH$_2$OH.

For use herein, the term EDOT-CH$_2$OH refers to a compound of Formula III:

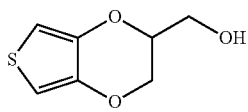

Formula III

In one embodiment, the present invention is directed to processes for preparing derivatized 3,4-alkylenedioxythiophene compounds comprising contacting a compound of Formula II:

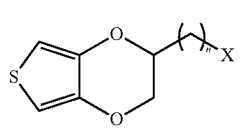

Formula II wherein X is halogen and n is from 1 to 4, with an inorganic hydroxide, alkali metal carboxylate, alkaline earth metal carboxylate, ammonium or alkylammonium carboxylate, alkaline earth metal alkoxide, alkali metal alkoxide, or ammonium or alkylammonium alkoxide, to provide a compound of Formula I wherein n is from 1 to 4:

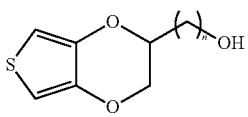

Formula I

In one embodiment, n is 1 and the derivatized 3,4-alkylendioxythiophene compound is EDOT-CH$_2$OH In one embodiment, the inorganic hydroxide is an alkali metal hydroxide, an alkaline earth metal hydroxide, or an ammonium or alkylammonium hydroxide. Exemplary alkali metal hydroxides include, for example, KOH, NaOH, or LiOH. Exemplary alkaline earth metal hydroxides include, for example, Mg(OH)$_2$ or Ca(OH)$_2$.

In one embodiment, the contacting step is performed in the presence of a catalyst. The catalyst can be any molecule capable of facilitating the synthesis reaction. In some exemplary embodiments, the catalyst is a crown ether. For use herein, the term crown ether refers to a macrocyclic polyether whose structure exhibits a conformation with a so-called hole capable of trapping cations by coordination with a lone pair of electrons on oxygen atoms. Each oxygen atom is bound between two of the carbons atoms and arranged in a ring. Exemplary crown ethers for use herein include 18-crown-6, 15-crown-5, 12-crown-4 or a combination thereof.

In one embodiment, the conversion of a compound of Formula II to a derivatized 3,4-alkylenedioxythiophene compound, such as a 3,4-alcohol, is by a substitution reaction. A substitution reaction involves replacement of a leaving group by another functional group. In one aspect, a substitution reaction entails reacting a compound of Formula II with an hydroxide salt in one or more polar aprotic solvents. In some exemplary embodiments, the one or more crown ethers, one or more cryptands, sodium iodide, or a combination thereof can be used as catalysts. The term cryptands refers to a macropolycyclic polyazo-polyether, where the three-coordinate nitrogen atoms provide the vertices of a three-dimensional structure. Exemplary cryptands include, for example, 4,7,13,16,21,24-hexaoxa-1,10-diazabicyclo[8.8.8]hexacosane.

In one embodiment, the conversion of a compound of Formula II to a derivatized 3,4-alkylenedioxythiophene compound, such as a 3,4-alkylenedioxythiophene alcohol, is by a two-step procedure. The first step is a substitution reaction using the salt of a carboxylic acid, e.g., sodium acetate, potassium acetate, ammonium acetate, sodium benzoate, potassium benzoate, and ammonium benzoate, in one or more polar aprotic solvents to form an organic ester. The ester can then be hydrolyzed to form the corresponding 3,4-alkylenedioxythiophene alcohol.

In one embodiment, an alkali metal alkoxide is used to convert the compound of Formula II to a 3,4-alkylenedioxythiophene alcohol, e.g., EDOT-CH$_2$OH. The alkali metal alkoxide can be used to form an ether that is then converted to a 3,4-dioxyalkylenthiophene alcohol, e.g., EDOT-CH$_2$OH, via one or more cleaving agents. Exemplary cleaving agents include, for example, zinc or acetic acid. Exemplary alkalki metal alkoxides include, for example, sodium allyloxide such as sodium 2-propen-1-oxide).

Also provided are processes for preparing a compound of Formula II

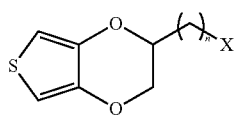

Formula II wherein X is halogen and n is from 1 to 4, comprising contacting a 3,4-alkylenedioxythiophene with a halo-1,2-alkanediol in the presence of an acid. In one embodiment, the halo-1,2-alkanediol has the formula CH$_2$(OH)CH(OH)(CH$_2$)$_n$X, where n is from 1 to 4. Exemplary acids include, but are not limited to, para-toluenesulfonic acid, methanesulfonic acid, trifluoromethanesulfonic acid, trifluoroacetic acid, sulfuric acid, or any combination thereof.

In one embodiment, n is 1 and the 3,4-alkylenedioxythiophene is contacted with 3-halo-1,2,-propanediol. In embodiments, wherein n is 2, 3, or 4, 3,4-alkylenedioxythiophene can be contacted with other halo-1,2,-alkanediols including, for example, 3-bromo-1,2-propanediol, 4-bromo-1,2-butanediol, 5-bromo-1,2-pentanediol, and the like. Halo-1,2,-alkanediols are readily available from commercial sources, such as Aldrich Company, Milwaukee, Wis., USA., can be synthesized according to methods known in the art (*Journal of Catalysis*, 208(2), 339-344, 2002; *Synthesis*, (4), 295-7, 1989), or through direct oxidation of ω-bromo-α-olefins using an oxidizing agent such as potassium permanganate or osmium tetroxide.

In one embodiment, the contacting step is performed in the presence of a solvent. Exemplary solvents include, but are not limited to aralkanes. In one embodiment of the present invention, the aralkane is toluene. Exemplary 3-halo-1,2-propanediols include 3-chloro-1,2-propanediol and 3-bromo-1,2-propanediol.

In one embodiment, provided are processes for preparing a derivatized 3,4-alkylenedioxythiophene comprising contacting 3,4-dihalothiophene, e.g., 3,4-dibromothiophene, with an alkoxide in the presence of copper and iodine reagents. In one embodiment, the 3,4-dialkoxythiophene is 3,4-dimethoxythiophene. Exemplary alkoxides include, but are not limited to, sodium or potassium methoxide. The copper and iodine reagents can be any compound capable of facilitating the synthesis reaction. In an exemplary embodiment, the reagents are copper(II) oxide and potassium iodide. (Both need to be present for the reaction to work.) In one embodiment, the contacting step is performed in the presence of a solvent. Exemplary solvents include, for example, alkanols. Exemplary alkanols include, for example, methanol. In one aspect, the process is carried out at reflux. In one embodiment, the reaction is conducted under an inert atmosphere of nitrogen, argon, or a combination thereof.

Accordingly, provided are methods for preparing derivatized 3,4-alkylenedioxythiophene compounds comprising contacting a 3,4-alkylenedioxythiophene with a halo-1,2-alkanediol in the presence of an acid to form a compound of Formula II

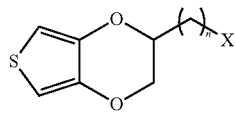

Formula II wherein X is halogen and n is from 1 to 4; and subsequently contacting a compound of Formula II with an inorganic hydroxide, alkali metal carboxylate, alkaline earth metal carboxylate, ammonium or alkylammonium carboxylate, alkali metal alkoxide, alkaline earth metal alkoxide, ammonium or alkylammonium alkoxide, to form a compound of Formula I:

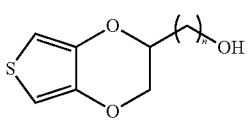

Formula I

In one aspect, the derivatized 3,4-alkylenedioxythiophene is prepared by contacting a 3,4-dihalothiophene with an alkoxide in the presence of copper and iodine reagents.

In one embodiment, provided are methods for preparing EDOT-CH$_2$OH comprising contacting 3,4-dialkoxythiophene with 3-halo-1,2-propanediol in the presence of an acid to form a compound of Formula IV:

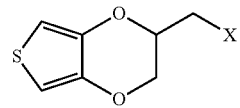

Formula IV wherein X is halogen; and subsequently contacting a compound of Formula IV with an inorganic hydroxide, ammonium or alkylammonium hydroxide, alkali metal carboxylate, alkaline earth metal carboxylate, ammonium or alkylammonium carboxylate, alkali metal alkoxide, alkaline earth metal alkoxide, ammonium or alkylammonium alkoxides, to form EDOT-CH$_2$OH. In one embodiment, the 3,4-dialkoxythiophene is prepared by contacting a 3,4-dihalothiophene with an alkoxide in the presence of copper and iodine containing reagents.

Also provided are compounds of Formula IV

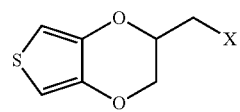

Formula IV wherein X is halogen.

Also provided are compounds of Formulas I, II, III, IV, V, and VI prepared by the processes described herein.

A representative synthetic scheme of the present invention is provided below as Scheme I. Scheme 1 demonstrates exemplary processes for the preparation of EDOT-CH$_2$OH ((2,3-dihydro-thieno[3,4-b][1,4]dioxin-2-yl)-methanol). The skilled practitioner will know how to make use of variants of these process steps. In this representative scheme, treatment of 3,4-dihalothiophene with an alkoxide base in the presence of copper(II) oxide and potassium iodide provides the corresponding 3,4-alkylenedioxythiophene. Reaction of 3,4-dialkoxythiophene with 3-halo-1,2-propanediol in the presence of an acid, such as para-toluenesulfonic acid, or the like, gives rise to a halomethyl derivatized EDOT. Subsequent reaction of the halo derivative with, for example, an alkali metal hydroxide, alkaline earth metal hydroxide, ammonium or alkylammonium hydroxide, alkali metal carboxylate, alkaline earth metal carboxylate, ammonium or alkylammonium carboxylate, alkali metal alkoxide, alkaline earth metal alkoxide, or ammonium or alkylammonium alkoxide converts the halo-EDOT to hydroxy-EDOT.

Scheme 1: Preparation of ((2,3-dihydro-thieno[3,4-b][1,4]dioxin-2-yl)-methanol)

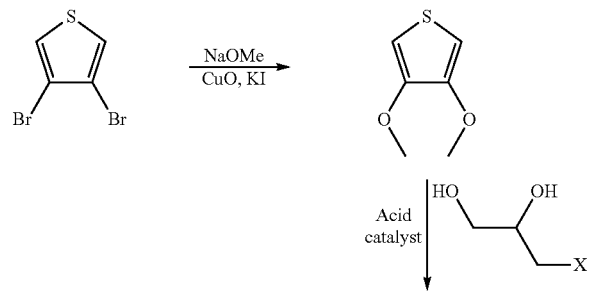

-continued

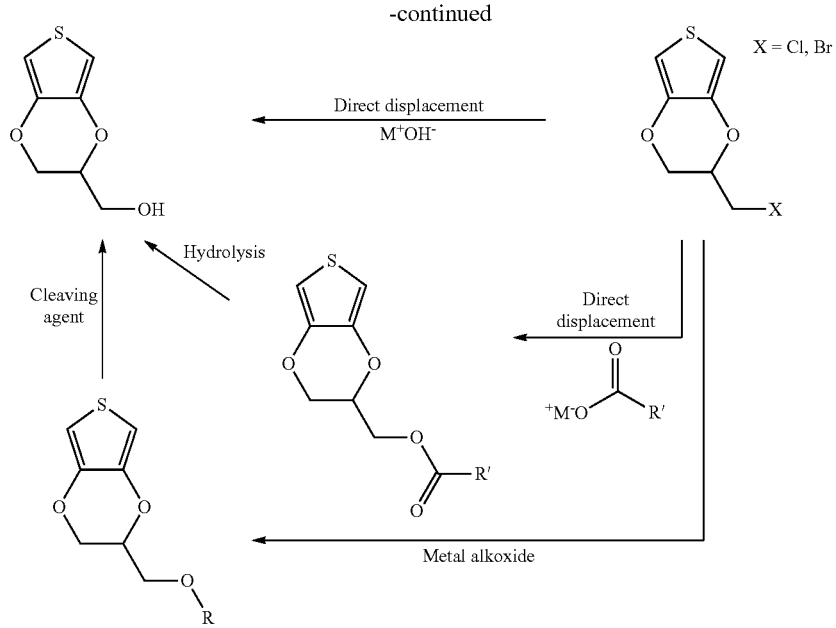

Compounds having Formulae V and VI can be prepared in a manner analogous to that for Compounds having Formula I and II, respectively. Compounds having Formula I or Formula V are referred to collectively as "derivatized 3,4-alkylenedioxythiophene compounds".

Also provided are compositions comprising derivatized 3,4-alkylenedioxythiophene compounds made by the processes described herein. These compositions can be in any form, including, but not limited to solutions, emulsions, colloids, and dispersions. In one aspect, the derivatized 3,4-alkylenedioxythiophene compounds are prepared using a synthetic scheme described herein Also provided are devices comprising derivatized 3,4-alkylenedioxythiophene compounds, such as EDOT-$CH_2OH$. In one embodiment, a device is provided that has at least one layer comprising at least one polymer comprising at least one monomer made by the processes described herein. In on embodiment, the device will further comprise at least one dispersion liquid, and optionally a processing aid, charge transporting material, or charge blocking material. The device can be, for example, for converting electrical energy into radiation, for detecting signals through electronic processes, or for converting radiation into electrical energy. In one aspect, the device will include one or more electronic components that include one or more organic semiconductor layers. In some exemplary embodiments, the device will further comprise coating materials for memory storage devices, antistatic films, biosensors, electrochromic devices, solid electrolyte capacitors, energy storage devices such as a rechargeable battery, electromagnetic shielding applications or combinations thereof.

As described in published application U.S. 2004/0254297 and copending U.S. Provisional Application No. 60/694,276, each of which is herein incorporated by reference in its entirety, poly(3,4-ethylenedioxythiophene)/fluorinated acid polymer ("PEDOT/FAP"), is an electrically conducting polymer (ECP) and is made by polymerization of 3,4-ethylenedioxythiophene (EDOT) in water and a fluorinated acid polymer. The fluorinated acid polymer can be any polymer which is fluorinated, and has acidic groups. Exemplary acidic groups include, for example, carboxylic acid groups, sulfonic acid groups, sulfonimide groups, phosphoric acid groups, phosphonic acid groups, or combinations thereof. The fluorinated acid polymer can be either soluble, or exist as a colloid in an aqueous media. An aqueous media refers to a mixture of liquid that has at least 40% water.

Electrically conducting polymer (ECP) of PEDOT/FAP has multiple utilities, including use as a buffer layer or hole-injection layer in organic electronic devices. Use of PEDOT/FAP in organic light emitting diodes has provided improved lifetime and efficiency for the devices. EDOT-$CH_2OH$ as prepared by the methods of the present invention can be used in place of EDOT to make PEDOT/FAP. The term of buffer layer or hole-injection layer refers to a material which is coated on an anode to facilitate hole injection from anode and hole transport through the layer.

Accordingly, in one embodiment, provided are methods of making electrically conductive polymers comprising a step of polymerizing EDOT-$CH_2OH$ or another derivatized 3,4-alkylenedioxythiophene compound described herein in an aqueous FAP solution or dispersion. In one aspect of the invention, the electrically conductive polymers can comprise copolymers of EDOT-$CH_2OH$ with at least one comonomer. The copolymer can be, for example, a block copolymer, a gradient copolymer, or a random copolymer. Examples of comonomers include, but are not limited to any oxidative polymerizable monomer such as pyrroles, anilines, thiophenes, substituted pyrroles, substituted anilines, substituted thiophenes, or combinations thereof.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Illustrative Electronic Devices, and finally Examples.

1. Definitions and Clarification of Terms

Before addressing details of embodiments described below, some terms are defined or clarified.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components of the invention. This is done merely for convenience and to give a general sense of the invention. This description should be read to include one or at least one and the singular also includes the plural unless it is obvious that it is meant otherwise.

The term "halogen" or "halo" refers to chlorine, bromine, fluorine, and iodine.

The term "organic electronic device" is intended to mean a device including one or more semiconductor layers or materials. Organic electronic devices include, but are not limited to: (1) devices that convert electrical energy into radiation (e.g., a light-emitting diode, light emitting diode display, diode laser, or lighting panel), (2) devices that detect signals through electronic processes (e.g., photodetectors photoconductive cells, photoresistors, photoswitches, phototransistors, phototubes, infrared ("IR") detectors, or biosensors), (3) devices that convert radiation into electrical energy (e.g., a photovoltaic device or solar cell), and (4) devices that include one or more electronic components that include one or more organic semiconductor layers (e.g., a transistor or diode).

The term "device" also includes coating materials for memory storage devices, antistatic films, biosensors, electrochromic devices, solid electrolyte capacitors, energy storage devices such as a rechargeable battery, and electromagnetic shielding applications.

The term "layer" is used interchangeably with the term "film" and refers to a coating covering a desired area. The area can be as large as an entire device or a specific functional area such as the actual visual display, or as small as a single sub-pixel. Films can be formed by any conventional deposition technique, including vapor deposition and liquid deposition. Liquid deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing.

The term "active" when referring to a layer or material is intended to mean a layer or material that exhibits electronic or electro-radiative properties. An active layer material may emit radiation or exhibit a change in concentration of electron-hole pairs when receiving radiation.

"Aralkane" refers to a moiety composed of an alkane bearing an aryl substituent or to a cycloalkane fused to an aryl ring and having from about 6 to about 20 carbon atoms (and all combinations and subcombinations of ranges and specific numbers of carbon atoms therein), with from about 6 to about 10 carbon atoms being preferred. Non-limiting examples include, for example, toluene, ethyl benzene, mesitylene, tetralin, cumene, cymene, methylnaphthalene, and diphenylmethane.

The term "colloid" or "colloidal" refers to the minute particles suspended in a continuous liquid medium, said particles having a nanometer-scale particle size. The term "colloid-forming" refers to substances that form minute particles when dispersed in a liquid medium, i.e., "colloid-forming" materials are not soluble in the liquid medium.

"Alkyl" refers to an optionally substituted, saturated straight, branched, or cyclic hydrocarbon radical having from about 1 to about 20 carbon atoms (and all combinations and subcombinations of ranges and specific numbers of carbon atoms therein). Alkyl groups include, but are not limited to, methyl, ethyl, n-propyl, isopropyl, n-butyl, isobutyl, t-butyl, n-pentyl, isopentyl, neopentyl, n-hexyl, isohexyl, 3-methylpentyl, 2,2-dimethylbutyl, and 2,3-dimethylbutyl.

"Alkoxide" refers to an alkyl-O— anion, wherein alkyl is as previously defined. Alkoxide is generally associated with a cationic counterion, such as Na+, K+, Li+, Mg++, Ca++, ammonium, alkylammonium, and the like on an equivalent charge basis. Exemplary alkoxides include, for example, methoxide, ethoxide, n-propoxide, i-propoxide, n-butoxide, and heptoxide.

"Alkanol" refers to alkyl alcohols, such as those provided by protonation of alkoxides, wherein alkyl is as previously defined.

"Halo" refers to a fluoro, chloro, bromo, or iodo moiety.

As used herein, the term "electrically conductive polymer" refers to any polymer or oligomer which is inherently or intrinsically capable of electrical conductivity without the addition of carbon black or conductive metal particles. The term "polymer" encompasses homopolymers and copolymers. The term "electrical conductivity" includes conductive and semi-conductive. In one embodiment, films made from the doped electrically conductive polymer have a conductivity of at least $10^{-7}$ S/cm Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below.

To the extent not described herein, many details regarding specific materials, processing acts, and circuits are conventional and may be found in textbooks and other sources within the organic light-emitting diode display, photodetector, photovoltaic, and semiconductive member arts.

2. Illustrative Electronic Devices

One illustration of an organic electronic device structure is shown in FIG. 1. The device 100 has an anode layer 110 and a cathode layer 160, and a photoactive layer 130 between them. Adjacent to the anode is a layer 120 comprising a hole injection layer derived from an electrically conducting polymer, for example, poly(EDOT-CH$_2$OH)/FAP of this invention. Optionally, a hole transporting layer (not shown in FIG. 1) is sandwiched between a hole injection layer 120 and a photoactive layer 130. Adjacent to the cathode is an electron transport layer 140 comprising an electron transport material. As an option, devices may use a further electron injection layer 150, next to the cathode.

The device 100 can include a substrate 105. The substrate 105 may be rigid or flexible, for example, glass, ceramic, metal, or plastic. When voltage is applied, emitted light is visible through the substrate 105. The anode layer 110 may be deposited on the substrate 105.

As used herein, the term, the charge injection refers to a material that facilitates hole injection from anode or electron injection from cathode.

As used herein, the term "photoactive" refers to a material that emits light when activated by an applied voltage (such as in a light-emitting diode or light-emitting electrochemical cell), or responds to radiant energy and generates a signal with or without an applied bias voltage (such as in a photodetector). An example of a photoactive layer is an emitter layer.

As used herein, the term "charge transport," when referring to a layer, material, member or structure, is intended to mean such layer, material, member or structure facilitates migration of such charge through the thickness of such layer, material, member, or structure with relative efficiency and small loss of charge, and is meant to be broad enough to include materials that may act as a hole transport or an electron transport material. The term "electron transport" or "hole transport" when referring to a layer, material, member or structure means such a layer or material, member or structure that promotes or facilitates migration of negative charge or positive charge, respectively, through such a layer or material into another layer, material, member or structure.

The term "charge blocking," when referring to a layer, material, member, or structure, is intended to mean such layer, material, member or structure reduces the likelihood that a charge migrates into another layer, material, member or structure. The term "electron blocking" when referring to a layer, material, member or structure is intended to mean such layer, material, member or structure that reduces that likelihood that electrons migrate into another layer, material, member or structure.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Kirk-Othmer Concise Encyclopedia of Chemical Technology, $4^{th}$ edition, p. 1537, (1999).

In certain embodiments, a charge transport layer, for example, the electron transport layer 140 comprises, but are not limited to, metal chelated oxinoid compounds, such as bis(2-methyl-8-quinolinolato)(para-phenyl-phenolato)aluminum(III) (BAlQ), tetra(8-hydroxyquinolato)zirconium (ZrQ), and tris(8-hydroxyquinolato)aluminum ($Alq_3$); azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthroline derivatives such as 9,10-diphenylphenanthroline (DPA) and 2,9-dimethyl-4,7-diphenyl-1,10-phenanthroline (DDPA); and any one or more combinations thereof. The optional electron injection layer 150 may be inorganic and comprise BaO, LiF, $Li_2O$, or the like.

In certain embodiments, the photoactive layer 130 comprises a photoactive material admixed with at least one tris (N-aryl-benzimidazole)benzene compound.

The other layers in the device can be made of any materials which are known to be useful in such layers. The anode 110, is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode 110 may also comprise an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

The optional hole transport layer, which is layer that facilitates the migration of positive charges through the layer into another layer of the electronic device, can include any number of materials. Examples of other hole transport materials have been summarized for example, in Kirk Othmer Encyclopedia of Chemical Technology, Fourth Edition, Vol. 18, p. 837 860, 1996, by Y. Wang. Both hole transporting molecules and polymers can be used. Commonly used hole transporting molecules include, but are not limited to: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl 4-N,N-diphenylaminostyrene (TPS), p-(diethylamino)benzaldehyde diphenylhydrazone (DEH), triphenylamine (TPA), bis[4(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N' tetrakis-(4-methylphenyl)-(1,1'-biphenyl)-4,4'-diamine (TTB), N,N'-bis(naphthalen-1-yl)-N,N'-bis-(phenyl)benzidine (α-NPB), and porphyrinic compounds, such as copper phthalocyanine. Commonly used hole transporting polymers include, but are not limited to, polyvinylcarbazole, (phenylmethyl)polysilane, polydioxythiophenes, polypyrroles, and polyanilines. It is also possible to obtain hole transporting polymers by doping hole transporting molecules such as those mentioned above into polymers such as polystyrene and polycarbonate.

In another embodiment, HTM comprises copolymer of arylamines with conjugated monomers. In another embodiment, the HTM polymers or copolymers comprises crosslinkable segments to render insolubility in the solvents of subsequent layer depositions. It is also possible to obtain hole transporting polymers by doping hole transporting molecules such as those mentioned above into polymers such as polystyrene and polycarbonate.

Any organic electroluminescent ("EL") material can be used as the photoactive material in layer 130. Such materials include, but are not limited to, small organic fluorescent compounds, fluorescent and phosphorescent metal complexes, conjugated polymers, and mixtures thereof. Examples of fluorescent compounds include, but are not limited to, pyrene, perylene, rubrene, coumarin, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, and mixtures thereof. Examples of conjugated polymers include, but are not limited to poly(phenylenevinylenes), polyfluorenes, poly(spirobifluorenes), polythiophenes, poly(p-phenylenes), copolymers thereof, and mixtures thereof.

In one embodiment of the device, the photoactive material is an organometallic complex. In one embodiment, the photoactive material is a cyclometalated complex of iridium or platinum. Complexes of iridium with phenylpyridine, phenylquinoline, or phenylpyrimidine ligands have been disclosed as electroluminescent compounds in Petrov et al., Published PCT Application WO 02/02714. Other organometallic complexes have been described in, for example, published applications US 2001/0019782, EP 1191612, WO 02/15645, and EP 1191614. Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in Synth. Met. (2001), 116 (1-3), 379-383, and Campbell et al., in Phys. Rev. B, Vol. 65 085210. Analogous tetradentate platinum complexes can also be used. These electroluminescent complexes can be used alone, or doped into charge-carrying hosts, as noted above. In one embodiment, the compounds are charge-carrying hosts admixed with other fluorescent or phosphorescent materials.

Examples of electron transport materials which can be used in the electron transport layer 140 may include at least one tris(N-aryl-benzimidazole)benzene compounds. These layers can optionally include a polymer, such as a polyfluorene or a polythiophene. Other suitable materials for layer 140 include metal chelated oxinoid compounds, such as tris (8-hydroxyquinolato)aluminum ($AlQ_3$); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof. The optional electron injection layer 150 may be inorganic and comprise BaO, LiF, $Li_2O$, or the like.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer and the cathode layer to lower the operating voltage.

An encapsulation layer 170 may be deposited over layer 160 to prevent entry of undesirable components, such as water and oxygen, into the device 100. Such components can have a deleterious effect on the organic components. In one embodiment, the encapsulation layer 170 is a barrier layer or film.

It is known to have other layers in organic electronic devices. For example, there can be a layer (not shown) between the anode 110 and hole injection layer 120 to facilitate positive charge transport and/or band-gap matching of the layers, or to function as a protective layer. Layers that are known in the art can be used. In addition, any of the above-described layers can be made of two or more layers. Alternatively, some or all of anode layer 110, the hole injection layer 120, the electron transport layer 140 and optional electron injection layer 150, and cathode layer 160, may be surface treated to increase charge carrier transport efficiency. The choice of materials for each of the component layers is preferably determined by balancing the goals of providing a device with high device efficiency with device operational lifetime.

The device can be prepared by a variety of techniques, including sequentially depositing the individual layers on a suitable substrate. Substrates such as glass, metal, and polymeric films can be used. Conventional vapor deposition techniques can be used, such as thermal evaporation, chemical vapor deposition, and the like. Alternatively, the organic layers can be applied by liquid deposition using suitable solvents. The liquid can be in the form of solutions, dispersions, or emulsions. Typical liquid deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing. any conventional coating or printing technique, including but not limited to spin-coating, dip-coating, roll-to-roll techniques, ink jet printing, screen-printing, gravure printing and the like.

In one embodiment, the different layers have the following range of thicknesses: anode 110, 500-5000 Å, in one embodiment 1000-2000 Å; hole injection layer 120, 50-2000 Å, in one embodiment 200-1000 Å; photoactive layer 130, 10-2000 Å, in one embodiment 100-1000 Å; layers 140 and 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

Although methods and materials similar or equivalent to those described herein can be used in the practice or testing of the present invention, suitable methods and materials are described below. All publications, patent applications, patents, and other references mentioned herein are incorporated by reference in their entirety and for all purposes.

EXAMPLES

Example A provides a method for the prior art method of synthesizing EDOT-$CH_2OH$ for comparative purposes. Examples 1 through 13 provide representative methods of the present invention.

Example A

Synthesis of 3,4-ethylenedioxythiophene methanol is adapted from the publication "Electropolymerization of and 3,4-ethylenedioxythiophene methanol in the presence of dodecylbenzenesulfonate", Lima A, Schottland P, Sadki A, Chevrot C; *Synth. Met.* 1998, 93, 33-41.

1) Synthesis of Diethyl Thiodiglycolate

In a 2-necked round bottom flask equipped with a reflux condenser and an equilibrium addition funnel 100 g (0.667 mol) thiodiglycolic acid was dissolved in 500 mL refluxing ethanol. The equilibrium addition funnel was charged with 40 mL concentrated sulfuric acid. The acid was added dropwise and the reaction refluxed overnight. Upon cooling the reaction to room temperature it was carefully poured into 600 mL water. The product was extracted with diethyl ether until the ether wash no longer contained the desired product. The organic extracts were washed with a saturated sodium bicarbonate solution three times. Upon drying with magnesium sulfate and solvent removal under reduced pressure a colorless oil was isolated (131.3 g, 95% yield). Structure and purity were confirmed by $^1H/^{13}C$ NMR and GC-MS.

2) Synthesis of Diethyl 3,4-dihydroxythiophene-2,5-dicarboxylate

In a 2 L two-necked flask equipped with a reflux condenser 175 g (2.57 mol) of sodium ethoxide was dissolved in 1200 mL anhydrous ethanol. The reaction was cooled to 0 C and a solution of 106 g (0.514 mol) diethylthioglycolate and 188 g (1.28 mol) diethyl oxalate in ethanol was added dropwise. Upon completion of the addition, the cooling bath was removed and the reaction heated to reflux overnight. The reaction was then cooled to room temperature and filtered. The resulting yellow solid was washed with ethanol and allowed to dry. The solid was split into two portions and each was added to a large Erlenmeyer flask with water to make a suspension upon stirring. Acidification with HCl provided a white solid. The solid was filtered and allowed to dry under vacuum to give 80 g (60% yield) of product as a white powder. Further material can be isolated by cooling the mother liquor and subsequent filtration. Structure and purity were confirmed by $^1H/^{13}C$ NMR and LC-MS.

3) Synthesis of Diethyl 2,3-dihydro-2-(hydroxymethyl)thieno[3,4-b][1,4]dioxine-5,7-dicarboxylate 7.7 mL (0.0902 mol) of epibromohydrin and 1.92 g (0.0139 mol) of potassium carbonate were dissolved in 100 mL water and added to a refluxing mixture of 16.11 g (0.0694 mol) diethyl 3,4-dihydroxythiophene-2.5-dicarboxylate in 350 mL ethanol. After heating to reflux for 1 hour, an additional 5.3 mL (0.0624 mol) epibromohydrin was added and the reaction heated to reflux overnight. Upon cooling to room temperature the reaction was concentrated by evaporation and then poured into 500 ml water. The mixture was acidified and then extracted with methylene chloride until the organic wash no longer indicated product was present. The organic fractions were washed with saturated brine then dried with magnesium sulfate. The solvent was removed under reduced pressure to give a yellow solid. Column chromoatography was performed using 60% ethyl acetate in hexane to give a 70:30 mixture of the product and propylene isomer in 55% yield as a white solid. Structure and purity were confirmed by $^1H/^{13}C$ NMR and LC-MS.

4) Synthesis of Diethyl-2-(hydroxymethyl)-2,3-dihydrothieno[3,4-b]-1,4-dioxine-5,7-dicarboxylic Acid In a 500 mL round bottom flask equipped with a reflux condenser 11.3 g (0.0357 mol) diethyl 2,3-dihydro-2-(hydroxymethyl)thieno[3,4-b][1,4]dioxine-5,7-dicarboxylate was combined with 12.0 g (0.214 mol) potassium hydroxide in 250 mL water. The reactin mixture was refluxed and the progress of the reaction tracked by TLC. Upon completion of the hydrolysis the reaction was concentrated to ~100 mL. The mixture was cooled to 0 C then acidified with concentrated HCl. After allowing to warm to room temperature overnight the white solid was filtered and washed with a small amount of water. Drying under high vacuum gave 8.5 g (90%) of product as a white solid. Structure and purity were confirmed by $^1H/^{13}C$ NMR and LC-MS.

5) Synthesis of Diethyl-2-(hydroxymethyl)-2,3-dihydrothieno[3,4-b]-1,4-dioxin-2-yl Methanol In a 100 mL round bottom flask, 14.0 g (0.053 mol) of finely powdered 2,3-dihydro-2-(hydroxymethyl)thieno[3,4-b]dioxine-5.7-dicarboxylic acid, 0.42 g copper(II) oxide, and 25 mL quinoline were combined. A reflux condenser was equipped and reaction flask purged with nitrogen. The mixture was heated to 225 C and the reaction traced by TLC. Once all starting material was consumed, the reaction was cooled to room temperature, diluted with ether and filtered. The ether was removed under reduced pressure. The crude product mixture was purified by column chromatography using 30% ethyl acetate in hexane. Upon removal of the solvent 4.4 g (48% yield) of a light yellow oil was isolated. Structure and purity were confirmed by $^1H/^{13}C$ NMR and GC-MS.

Example 1

Synthesis of Chloromethyl-3,4-ethylenedioxythiophene for Conversion to EDOT-MeOH 1) 3,4-dimethoxythiophene Synthesis from 3,4-dibromothiophene for the Improved EDOT-MeOH Synthesis Sodium methoxide was prepared by slow addition of small cubes of sodium metal (25 g, 1.05 mol) to ice bath cooled anhydrous methanol (600 mL) in a 1 L 3-necked flask equipped with a reflux condenser under a nitrogen blanket. Between additions of the sodium it was covered in kerosene to exclude moisture. After complete dissolution of the sodium, 50 g (0.207 mol) of 3,4-dibromothiophene, 16.5 g (0.207 mol) copper (II) oxide, and 1.37 g (0.00827 mol) potassium iodide was added to the reaction mixture. The reaction was refluxed for three days. The reaction was then cooled to room temperature and filtered through a sintered glass fritted funnel. The resulting solid was rinsed with ether and the filtrate was poured into 500 mL water. The solution was then extracted with ether. The organic fractions were combined and dried with magnesium sulfate. Solvent removal gave a light yellow oil. Vacuum distillation gave 26.2 g of a clear, colorless oil whose structure and purity were confirmed by $^1H$ and $^{13}C$ NMR and GC-MS. Yield was 88% of theoretical.

2) Synthesis of 2-(chloromethyl)-2,3-dihydrothieno[3,4-b][1,4]dioxine

Under a nitrogen atmosphere in a 500 mL round bottom flask equipped with a reflux condenser, 20.0 g (0.139 mol) dimethoxythiophene, 17.8 g (0.161 mol) 3-chloro-1,2-propanediol, and 5 g p-toluenesulfonic acid was dissolved in 350 mL toluene. The reaction was then heated to ~90 C overnight. At this time TLC indicated consumption of starting material. After cooling the reaction mixture was concentrated to ~100 mL and poured into saturated potassium carbonate solution. The mixture was extracted with DCM and the combined extracts were dried with magnesium sulfate. Solvent removal gave a dark oil that was purified by column chromatography using 3:1 hexanes/DCM. Solvent removal gave the product as a white solid. Structure and purity were confirmed by $^1H/^{13}C$ NMR and LC-MS.

Example 2

Conversion of 3,4-dimethoxythiophene to 2-(bromomethyl)-2,3-dihydrothieno[3,4-b][1,4]dioxine Under nitrogen, 20.0 g (0.139 mol) dimethoxythiophene, 25.0 g (0.161 mol) 3-bromo-1,2-propanediol, and 5 g p-toluenesulfonic acid was combined with 350 mL toluene in a 500 mL round bottom flask equipped with a reflux condenser and stir bar. The reaction mixture was sparged with nitrogen for 30 minutes then heated to 100 C overnight. Upon cooling to room temperature the reaction mixture was concentrated to ~100 mL and poured into saturated potassium carbonate solution. The resulting solution was extracted with DCM. The combined extracts were washed with brine, then dried with magnesium sulfate. Solvent removal gave a black oil. The crude material was purified by column chromatography using 3:1 hexanes/DCM. Solvent removal gave a white solid that was dried under high vacuum overnight to give 18.6 g of material. The structure and purity were confirmed by $^1H/^{13}C$ NMR and GC-MS. Yield was 57% of theoretical.

Example 3

Synthesis of (2,3-dihydrothieno[3,4-b][1,4]dioxin-3-yl)methanol from (2,3-dihydrothieno[3,4-b][1,4]dioxin-2-yl)methyl Acetate 1) Synthesis of (2,3-dihydrothieno[3,4-b][1,4]dioxin-2-yl)methyl Acetate (EDOT-MeOAc)

In a 50 mL Schlenk tube 1.00 g of to 2-(bromomethyl)-2,3-dihydrothieno[3,4-b][1,4]dioxine was combined with 0.5 g (0.0051 mol) potassium acetate and 25 mL DMSO. The tube was sealed and stirred for 1 h at 100 C. At this time TLC indicated complete consumption of starting material. The reaction was poured into water and extracted with ether. After removing the ether under reduced pressure column chromatography was performed using 90% methylene chloride in hexane to isolate a light yellow oil in 90% yield. The structure and purity were confirmed by $^1H/^{13}C$ NMR and GC-MS.

2) Synthesis of (2,3-dihydrothieno[3,4-b][1,4]dioxin-3-yl)methanol (EDOT-MeOH)

In a 25 mL round bottom flask equipped with a reflux condenser 0.64 g (0.0030 mol) of (2,3-dihydrothieno[3,4-b][1,4]dioxin-2-yl)methyl acetate was combined with 50% NaOH in water. The reaction was refluxed overnight and then cooled to room temperature. It was then poured into an Erlenmeyer flask filled with 100 mL water. The mixture was acidified then extracted with DCM. The solvent was removed under reduced pressure and column chromatography (7:3 hexanes/ethyl acetate) was performed to give 0.46 g (90%) of product. The structure was confirmed by LC-MS and $^1H/^{13}C$ NMR.

Example 4

Synthesis of EDOT-MeOH from EDOT-Methyl-Benzoate

1) Synthesis of (2,3-dihydrothieno[3,4-b][1,4]dioxin-3-yl)methyl Benzoate

In a 100 mL round bottom flask 9.00 g (0.0382 mol) 2-(bromomethyl)-2,3-dihydrothieno[3,4-b][1,4]dioxine, 6.39 g (0.0459 mol) ammonium benzoate, and 55 g DMSO were combined. A reflux condenser was equipped and the reaction was heated to 100 C overnight. After cooling to room temperature, the reaction mixture was poured into water and the product was extracted with methylene chloride. The organic fractions were combined and the solvent removed under reduced pressure. Purification by column chromatography provided 7.5 g (71% yield) of a white solid whose structure was confirmed by 1H/13C NMR and LC-MS.

2) Synthesis of (2,3-dihydrothieno[3,4-b][1,4]dioxin-3-yl)methanol

In a 100 mL round bottom flask, 7.5 g (0.027 mol) (2,3-dihydrothieno[3,4-b][1,4]dioxin-3-yl)methyl benzoate was dissolved in a minimal amount of warm ethanol and dropwise added to a refluxing solution of 4.58 g (0.081 mol) potassium hydroxide in 50 mL water. After heating overnight, the reaction was cooled to room temperature and acidified to pH 7 by dropwise addition of concentrated hydrochloric acid. The reaction mixture was extracted with methylene chloride. The organic fractions were combined and the solvent removed under reduced pressure. Purification by column chromatography provided 3.95 g (85% yield) of (2,3-dihydrothieno[3,4-b][1,4]dioxin-3-yl)methanol. Structure was confirmed by 1H/13C NMR and LC-MS.

Example 5

Synthesis of EDOT-MeOH from Chloromethyl-EDOT (from a Carboxylic Acid Salt to Form an Ester and Subsequent Cleaving of the Ester Linkage with Potassium Hydroxide)

Chloromethyl-EDOT will be reacted with a carboxylic acid salt, e.g. Acetate, heated to 100-140° C. in a polar/aprotic solvent, e.g. DMF, DMAc or DMSO. The resulting ester will then be cleaved easily by using a typical base saponification, e.g. 1% KOH in MeOH/H$_2$O or with transesterification using an Acid or a base in the presence of MeOH.

Example 6

Synthesis of EDOT-MeOH from Chloromethyl-EDOT (Using Alkoxides and Subsequent Cleaving of the Ether Linkage Formed)

Sodium or sodium hydride will be used to form the alkoxide of any of the following alcohols:

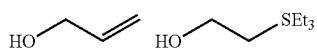

Chloromethyl-EDOT will then be reacted with the alkoxide to yield the ether. These ether functionalities will then be easily cleaved by using the well-documented appropriate agent, yielding EDOT-MeOH.

Example 7

Synthesis of EDOT-MeOH from Bromomethyl-EDOT (In Situ Generation of Iodomethyl-EDOT to be Reacted with KOH)

In a round bottom flask, 1 g Bromomethyl-EDOT will be dissolved in acetone. A catalytic amount of sodium iodide will then be added. Solid KOH would then be added along with a small portion of DI Water. The resulting precipitate should be KCl, yielding the desired product.

Example 8

Synthesis of EDOT-MeOH from Bromomethyl-EDOT (Direct Reaction with KOH)

Bromomethyl-EDOT will be dissolved in a polar organic and then subjected to nucleophilic attack by OH$^-$. Isolation would involve water extraction and other standard practices.

Example 9

Synthesis of EDOT-MeOH from Bromomethyl-EDOT (Direct Reaction with Alkali Metal Hydroxide, e.g. KOH, with a Catalytic Amount of Appropriate Crown Ether, e.g. 18-Crown-6)

Bromomethyl-EDOT will be susceptible to nucleophilic attack with no "pre-derivitzation" required. This compound would be dissolved in a polar organic and then subjected to nucleophilic attack by OH$^-$ in the presence of a catalytic amount of the proper crown ether, e.g. if using NaOH, 15-Crown-5 would be used. Isolation will involve water extraction and other standard practices.

Example 10

Solubility Comparison Between EDOT-MeOH and EDOT

EDOT (2,3,-dihydrothieno[3,4-b]-1,4-dioxin) monomer purchased from Aldrich Advance Science Company (Milwaukee, USA) and EDOT-MeOH made in Example 5 were tested for solubility in water at room temperature which is about 23° C. EDOT has solubility less than 0.4% (w/w), but EDOT-MeOH has solubility of 1.4% (w/w). The improvement is more than sufficient to facilitate polymerization at the concentration illustrated in Example 11.

Example 11

Illustration of EDOT-MeOH Polymerization in the Presence of Nafion®, a perfluoroethylene-ether-sulfonic Acid, and Use of the Electrically Conducting for OLEDs 1) Polymerization of EDOT-MeOH in the Presence of Nafion®, poly(tetrafluoroethylene)/perfluoroethersulfonic Acid The Nafion® dispersion at 25% (w/w) having EW1050 was made using a procedure similar to the procedure in U.S. Pat. No. 6,150,426, Example 1, Part 2, except that the temperature was approximately 270° C. It was then diluted with water to form a 13.2% (w/w) dispersion for the polymerization. EDOT-MeOH used in this example was made according to the procedure in Example 5.

In a 500 mL reaction kettle were put 57.4 g of 13.2% solid content aqueous Nafion® dispersion (7.23 mmol SO$_3$H groups), 99.0 g water, and 130 μL of 37% HCl (1.62 mmol). While the mixture was stirred at 200 RPM using an overhead stirrer fitted with a double stage propeller blade, a stock solution of 0.65% iron(III)sulfate in water was made and 2.11 g of the solution was added to the kettle. To the mixture, 10.8 g (3.318 mmol) sodium persulfate pre-dissolved in 10 g water, and 0.548 g (3.184 mmol) EDOT-MeOH pre-dissolved in 35 g water were added. The addition was started from separate syringes using addition rate of 0.71 mL/h for Na$_2$S$_2$O$_8$/water and 2.5 mL/h for EDOT-MeOH water while continuously stirring at 200 RPM. The addition was accomplished by placing each solution in a syringe connected to a Teflon® tube. The end of the Teflon® tube was placed above the reaction mixture such that the injection involved individual drops falling from the end of the tube such that the injection was gradual. Once addition was complete, the reaction mixture was allowed to proceed for another 14.5 hours before termination by adding 15 g Lewatit® S100 (a trade name from Bayer, Pittsburgh, Pa., for sodium sulfonate of crosslinked polystyrene) and 15 g Lewatit® MP62 WS (a trade from Bayer Company, Pittsburgh, Pa., for free base/chloride of tertiary/quaternary amine of crosslinked polystyrene). The two resins were washed first before use with deionized water separately until there was no color in the water. The resin treatment was allowed to proceed for 11.5 hrs while being stirred at 120 RPM. The resulting slurry was then suction-filtered through a Whatman #4 filter paper. The poly (EDOT-MeOH)/Nafion® dispersion is blue in color, which is the typical color for having electrical conductivity. The dispersion is stable and has pH of 4.2 and solid percentage was measured to be 3.92% (w/w). Electrical conductivity of thin films cast from the dispersion and baked in air at 130° C. for 10 minutes is measured to be $1.3 \times 10^{-2}$ S/cm at room temperature.

2) Use of Poly(EDOT-MeOH)/Nafion® as a Hole Injection Layer (HIL) for Fabrication of Organic Light Emitting Diodes (OLEDs) Using Polymeric Green Emitter and Diode Performance;

The Poly(EDOT-MeOH)/Nafion® dispersion made in section 1 of Example 11 was spin-coated on glass/ITO backlight substrates (30 mm×30 mm). Each ITO substrate having ITO thickness of 100 to 150 nm consists of 3 pieces of 5 mm×5 mm pixels and 1 piece of 2 mm×2 mm pixel for light emission. Once spin-coated on ITO substrates, the films were baked first at 130° C. in air for 10 minutes and then at 200° C. for 10 minutes. The thickness of the layer after baked was 185 nm. The Poly(EDOT-MeOH)/Nafion® layer was top-coated with approximately 74 nm thick film of Lumination Green 1303 electroluminescence polymer from Dow Chemicals (from 1% w/v solution in p-Xylene) in air. Following the baking of the electroluminescent film at 130° C. in a dry box for 30 minutes, a cathode consisting of 3 nm of Ba and 250 nm of Al was thermally evaporated at pressure less then $4 \times 10^{-6}$ Torr. Encapsulation of the devices was achieved by bonding a glass slide on the back of the devices using an UV-curable epoxy resin.

Table 1 shows light emitting device efficiency 200, 500, 1,000 and 2,000 nits (cd/m$^2$). The data shows that efficiency rises very rapidly at low luminance and is about the same from 200 cd/m$^2$ to 2,000 cd/m$^2$.

TABLE 1

| | Lumination Green 1303 Device Efficiency | | | |
|---|---|---|---|---|
| | 200 (cd/m$^2$) | 500 (cd/m$^2$) | 1,000(cd/m$^2$) | 2,000 (cd/m$^2$) |
| Efficiency (cd/A) | 9.9 ± 3.4 | 10.2 ± 4.2 | 10.2 ± 4.1 | 10.4 ± 3.6 |

What is claimed is:

1. A process for preparing a compound of Formula I comprising the steps of i) contacting a 3,4-dialkoxythiophene with a halo-1,2-alkanediol in the presence of an acid to form a compound of Formula II:

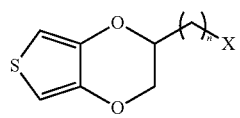

Formula II wherein X is halogen and n is from 1 to 4; and ii) contacting a compound of Formula II with an inorganic hydroxide, alkali metal carboxylate, alkaline metal carboxylate, ammonium or alkylammonium carboxylate, alkali metal alkoxide, alkaline metal alkoxide, ammonium or alkylammonium alkoxide, to form a compound of Formula I wherein n is from 1 to 4:

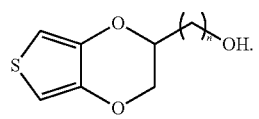

Formula I

2. The process of claim 1 wherein the 3,4-dialkoxythiophene is prepared by contacting a 3,4-dihalothiophene with an alkoxide in the presence of a copper and iodine containing reagents.

3. The process of claim 2 wherein the step of contacting is performed under an inert atmosphere of argon or nitrogen.

4. The process of claim 2 wherein the step of contacting a 3,4-dihalothiophene with an alkoxide is performed in the presence of a solvent.

* * * * *